United States Patent [19]

Borror et al.

[11] 4,181,660

[45] Jan. 1, 1980

[54] 3-SUBSTITUTED BENZ[D]ISOTHIAZOLE-1,1-DIOXIDES

[75] Inventors: Alan L. Borror, Lexington; Louis Cincotta, Andover; Ernest W. Ellis, Carlisle; James W. Foley, Andover; Marcis M. Kampe, Brookline, all of Mass.

[73] Assignee: Polaroid Corporation, Cambridge, Mass.

[21] Appl. No.: 836,024

[22] Filed: Sep. 23, 1977

[51] Int. Cl.$^2$ ............... C07D 275/06; C07D 417/10; C07F 7/18
[52] U.S. Cl. .................................. 548/110; 252/300; 548/207
[58] Field of Search ........................... 260/304 A, 301

[56] References Cited

PUBLICATIONS

Abramovitch, R. A. et al., J. Chem. Soc., Perkin Trans I, 22, pp. 2589–2594 (1974).
Haslam, E., "Protection of Catechols", Chap. 4, *Protective Groups in Organic Chemistry*, Plenum Press, N.Y. (1974).
Clauss, K. et al., Justus Liebigs, Ann. Chem., 1974, vol. 4, p. 569.

*Primary Examiner*—Alton D. Rollins
*Assistant Examiner*—Lisa Jones
*Attorney, Agent, or Firm*—Sybil A. Campbell

[57] ABSTRACT

This invention relates to 3-(phenyl/naphthyl)-benz[d]isothiazole-1,1-dioxides wherein the 3-phenyl or the 3-naphthyl group is substituted in the para position with hydroxy blocked with certain protecting groups. These compounds are useful as intermediates in the synthesis of certain 3,3-disubstituted-2,3-dihydrobenz[d]isothiazole-1,1-dioxide dyes which find utility, for example, as photographic optical filter agents and filter agent precursors.

23 Claims, No Drawings

3-SUBSTITUTED BENZ[d]ISOTHIAZOLE-1,1-DIOXIDES

BACKGROUND OF THE INVENTION

1. Field of the Invention

This invention relates to certain 3-substituted-benz[d]isothiazole-1,1-dioxides, and in particular, it relates to 3-(carbocyclic aryl)-benz[d]isothiazole-1,1-dioxides wherein the carbocyclic aryl group is substituted in the para position with certain -OP groups.

2. Description of the Prior Art

Though various 3-substituted-benz[d]isothiazole-1,1-dioxides have been disclosed, only a few 3-aryl derivatives are known. P. Fritsch, Ber., 29, p. 2290 (1896) reported that the 3-phenyl derivative was obtained by the reaction of 3-chlorobenz[d]isothiazole-1,1-dioxide (saccharin pseudochloride) and benzene under Friedel-Crafts conditions. The 3-(p-dimethylaminophenyl) derivative was prepared similarly. The 3-(p-chlorophenyl) derivative was obtained by the treatment of ammonium 2-(4'-chlorobenzoyl)benzenesulfonate with phosphorus pentachloride as reported by Z. Horii, Jap. Pat. Nos. 10,131/1964 and 8832/1964. R. A. Abramovitch et al, J. Chem Soc., Perkin Trans. I, 22, p. 2589 (1974) reported that the reaction of alkyl- and aryllithium compounds with 3-1 -oxo-2,3-dihydrobenz[d]isothiazole-1,1-dioxide (saccharin) in tetrahydrofuran at −78° C. gave the corresponding 3-alkyl or 3-aryl derivatives exclusively and prepared the 3-phenyl, 3-(o-tolyl), 3-(p-methoxyphenyl) and 3-(2-pyridyl) derivatives in this manner. The latter authors also reported that the 3-phenyl derivative was prepared by the treatment of saccharin with two equivalents of phenylmagnesium bromide in tetrahydrofuran at ambient temperature.

Copending U.S. patent application Ser. No. 836,010 of Stanley M. Bloom, Alan L. Borror and James W. Foley filed concurrently herewith is directed to a method of synthesizing 3,3-disubstituted-2,3-dihydrobenz[d]isothiazole-1,1-dioxides possessing a carbonyl group in the 2-position. Depending upon the carbonyl group and the 3,3 substituents, the products of the synthesis may be employed as pH-sensitive indicator dyes, antihalo dyes or photographic optical filter agents. As disclosed and claimed therein, the method of preparing these compounds comprises reacting a 3-(4'-OP-1'-phenyl/4'-OP-1'-naphthyl)-3-(phenyl/naphthyl)-2,3-dihydrobenz[d]isothiazole-1,1-dioxide wherein P is a protecting group compatible with organometallic reagents and a carboxylic acid halide in the presence of pyridine to yield the corresponding 2-carbonyl derivative. Optionally, the acylation may be carried out by sequentially reacting the said isothiazole compound with an alkali metal hydride to give the corresponding 2-alkali metal salt followed by reaction with the selected carboxylic acid halide. The acylated compound thus prepared is then treated with acid to remove the protecting group and yield the product.

The 3-(4'-OP-1'-phenyl/4'-OP-1'-naphthyl)-3-(phenyl/naphthyl)-2,3-dihydrobenz[d]isothiazole-1,1-dioxides employed as intermediates in the above method may be synthesized by reacting a 3-(4'-OP-1'-phenyl/4'-OP-1'-naphthyl)benz[d]isothiazole-1,1-dioxide and a phenyllithium or a naphthyllithium reagent as disclosed and claimed in copending U.S. patent application Ser. No. 836,008 of Alan L. Borror, Louis Cincotta, James W. Foley and Marcis M. Kampe filed concurrently herewith. The 3-(4'-OP-1'-phenyl/4'-OP-1'-naphthyl)benz[d]isothiazole-1,1-dioxide is prepared by converting a blocked 4-halophenol or a blocked 4-halo-1-naphthol to the corresponding Grignard or lithium reagent and then reacting this reagent with, e.g., saccharin or saccharin pseudo-chloride.

As discussed in the aforementioned applications, the protecting groups selected for preparing the blocked phenols or 1-naphthols should be compatible with organolithium and Grignard reagents and should protect the hydroxyl group against reaction under the conditions encountered in the synthesis of the aforesaid intermediates and in the subsequent steps in the synthesis of the products. In addition, the protecting group selected should be capable of being easily removed under neutral or weakly acid conditions to regenerate the hydroxyl group and yield the desired product. Though various blocking groups previously proposed for protecting hydroxyl groups in metalation reactions may be employed in the above-described procedures, certain blocking groups have only limited utility. For example, alkyl protecting groups, such as, methyl may be used only in those instances where they may be removed without removal of the 2-carbonyl substituent of the isothiazole ring.

The present invention is concerned with 3-substituted-benz[d]isothiazole-1,1-dioxides derived from phenols or 1-naphthols blocked with certain protecting groups which are compatible and stable in the presence of organometallic reagents and yet readily removed under neutral or weakly acid conditions to regenerate the hydroxyl group.

SUMMARY OF THE INVENTION

It is, therefore, the primary object of the present invention to provide novel 3-(4'-OP-1'-phenyl/4'-OP-1'-naphthyl)benz[d]isothiazole-1,1-dioxides wherein P represents certain protecting groups which compounds are useful as intermediates in the synthesis of the aforementioned 3,3-disubstituted-2,3-dihydrobenz[d]isothiazole-1,1-dioxides possessing a carbonyl group in the 2-position of the isothiazole ring.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

According to the present invention, 3-(phenyl/naphthyl)-benz[d]isothiazole-1,1-dioxides are provided wherein the 3-phenyl or the 3-naphthyl group is substituted in the 4'-position with hydroxyl blocked with certain protecting groups which compounds will be defined with greater particularity hereinafter.

For a fuller understanding of the nature and objects of the invention, reference should be had to the following detailed description.

DESCRIPTION OF THE PREFERRED EMBODIMENTS

Specifically, the compounds of the present invention may be represented by the formula:

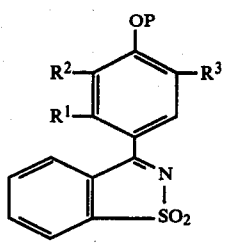

wherein $R^1$ is hydrogen, alkyl, alkoxy or -OP; $R^2$ and $R^3$ each are hydrogen, alkyl, alkoxy, chloro or fluoro; $R^1$ and $R^2$ taken together represent the carbon atoms necessary to complete a fused benzene ring; and P is methoxymethyl, 2'-tetrahydropyranyl or dimethyl-t-butylsilyl. Ordinarily, the alkyl groups and the alkoxy groups comprising $R^1$, $R^2$ and $R^3$ are lower alkyl having 1 to 4 carbon atoms and lower alkoxy having 1 to 4 carbon atoms.

Specific examples of compounds within the scope of the present invention are as follows:

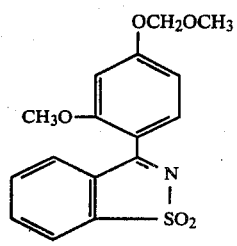

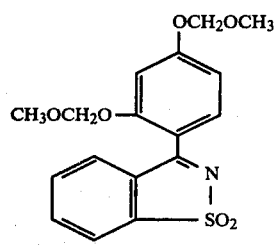

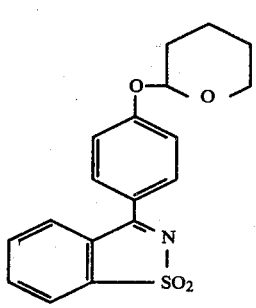

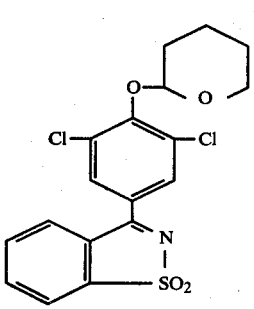

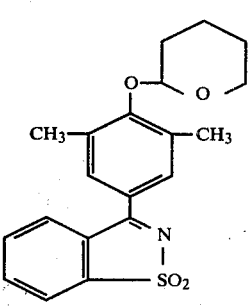

-continued
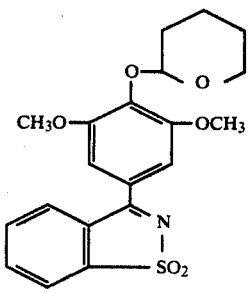 (10)
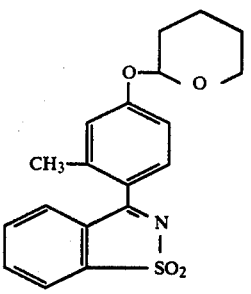 (11)
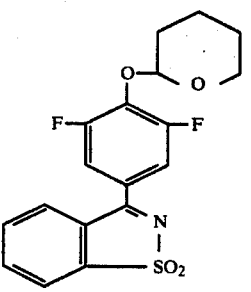 (12)
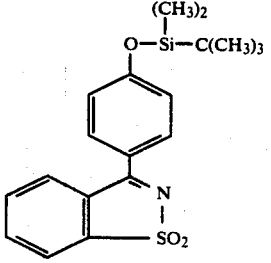 (13)
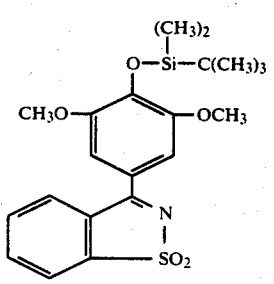 (14)
-continued
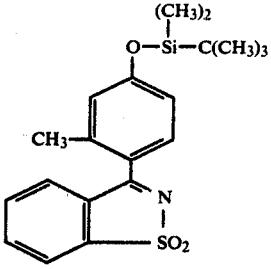 (15)
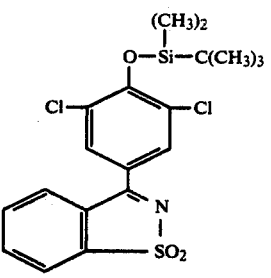 (16)
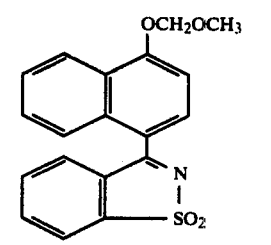 (17)
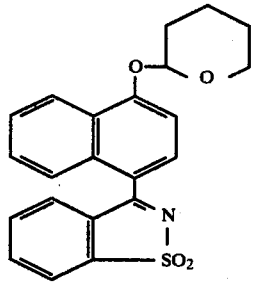 (18)
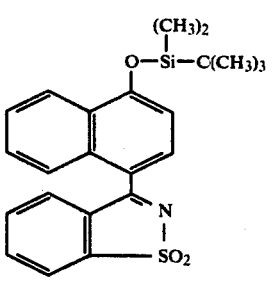 (19)
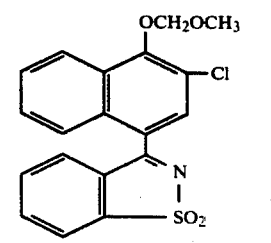 (20)

To prepare the compounds of the present invention, the selected 4-halophenol or 4-halo-1-naphthol is converted to the corresponding blocked compound by methoxymethylation as described, for example, by Kaoru Fuji et al, Synthesis, 4, pp. 276–277 (1975), by tetrahydropyranylation as described, for example, by William E. Parham et al, J. Amer. Chem. Soc., 70, pp. 4187–4189 (1948) or by silylating with dimethyl-t-butyl-silyl chloride in the presence of imidazole as described by E. J. Corey et al, J. Amer. Chem Soc., 94, pp. 6190–6191 (1972). The blocked compound thus prepared is then converted to the corresponding 4-lithium derivative by reaction with n-butyllithium or lithium metal. The halo substituent may be chloro, bromo or iodo when lithium metal is employed and is either bromo or iodo when a lithium exchange reaction is employed. The lithium derivative is then reacted with saccharin, saccharin pseudo-chloride or the lithium salt of saccharin to yield the corresponding 3-substituted-benz[d]isothiazole-1,1-dioxide as illustrated in the following reaction sequence using the saccharin lithium salt.

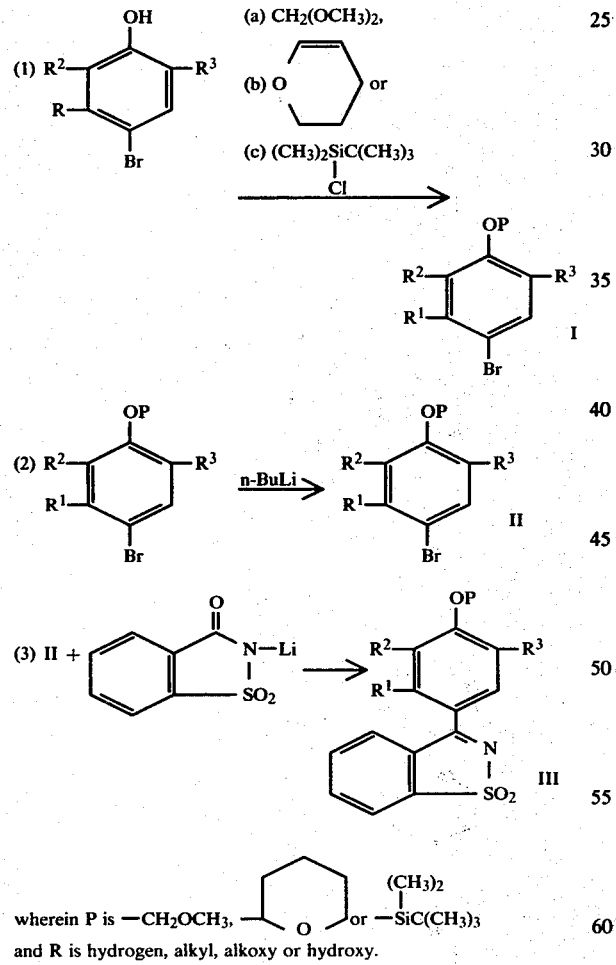

and R is hydrogen, alkyl, alkoxy or hydroxy.

The compounds of the present invention also may be prepared by reacting the blocked 4-halophenol or 4-halo-1-naphthol wherein halo is chloro, bromo or iodo with magnesium metal to form the corresponding Grignard reagent which is then reacted with saccharin, the N-lithium salt of saccharin or saccharin pseudo-chloride as illustrated below using the pseudo-chloride.

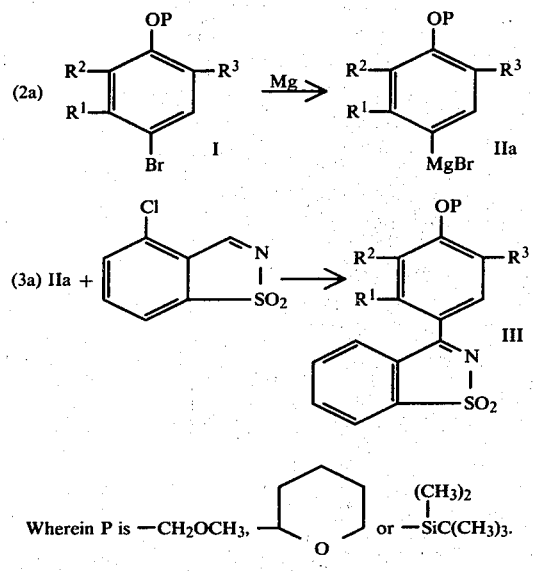

The 4-halophenols and 4-halo-1-naphthols used in step 1, if not commercially available, may be prepared by methods known in the art by reacting the selected phenol or 1-naphthol with, for example, chlorine or bromine with or without a catalyst, N-bromosuccinimide or iodinemonochloride.

The following examples are given to further illustrate the present invention and are not intended to limit the scope thereof.

EXAMPLE 1

Preparation of the Compound of Formula (2)

(i) Into a 2 liter three neck flask, fitted with a mechanical stirrer, nitrogen inlet and a dropping funnel, was placed 700 ml. of dry chloroform. The flask was immersed in an ice-water bath. Powdered phosphorus pentoxide (300.0 g.) was added to the vigorously stirred, cold chloroform. To this mixture was added over a 1 hour period a solution of 4-bromo-2,6-dimethylphenol (201.0 g.) in 400 ml. of dry dimethoxymethane. During this time the phosphorus pentoxide powder fused into an amorphous mass and stirring became difficult. TLC analysis (9:1 petroleum ether-ethyl acetate on silica gel) indicated that much unreacted starting phenol was still present. The temperature of the reaction mixture was allowed to rise to about 25° C. Additional 50 g. increments of phosphorus pentoxide were added to the stirred reaction mixture every 30–45 minutes until TLC analysis indicated the absence of starting phenol. The organic layer was decanted, washed with two 250 ml. portions of aqueous 10% sodium hydroxide and dried over calcium sulfate. The solvent was removed under reduced pressure leaving a pale yellow oil which was distilled from 25 g. of anhydrous potassium carbonate to give 220.0 g. of 4-bromo-2,6-dimethylmethylenemethoxyphenol ether as a colorless oil (boiling point 112° C. and 0.5 mm Hg).

(ii) 4-Bromo-2,6-dimethyl-methylenemethoxyphenyl ether (85.04 g.; 0.347 mole) was dissolved in approximately 800 ml. of tetrahydrofuran. The solution was cooled to −75° C. under a nitrogen blanket, and 2.4 M n-butyllithium in hexane (144.8 ml; 0.346 mole) was added dropwise. Addition was completed within a 2 hour period giving a white slurry.

(iii) Saccharin (61.2 g; 0.334 mole) was dissolved in 600 ml. of dry tetrahydrofuran, and the solution was cooled to approximately −75° C. 2.4 M n-butyllithium in hexane (130.4 ml; 0.311 mole) was slowly added dropwise to the cooled solution under a nitrogen blanket. The temperature was not allowed to rise above −70° C. Addition was completed in about 90 minutes, giving a clear, very pale yellow solution.

(iv) The yellow solution obtained in step (iii) was slowly added (over a 3 hour period) to the white slurry obtained in step (ii) while keeping the temperature at −70° C. During this time the solids disappear giving a clear, caramel colored reaction mixture that first tends to darken with time and then gradually lightens. The reaction mixture was allowed to come to room temperature overnight and then was treated with 36.0 g. of ammonium chloride in 250 ml. of water, while cooling in an ice-water bath. The organic portion was decanted and dried over anhydrous calcium sulfate. The solvent was removed under reduced pressure to give a pink colored oil that became solid or standing in open air. The solid was recrystallized twice from 1-propanol, washed with a 60:40% mixture of petroleum ether-tetrahydrofuran at −40° C. and dried under vacuum to give 68.0 g. of the title compound as a white, crystalline solid.

EXAMPLE 2

Preparation of the Compound of Formula (2)

Dry tetrahydrofuran (10–15 ml.) was added to magnesium turnings (0.20 g.) under nitrogen. A solution of 4-bromo-2,6-dimethyl-methyleneomethoxy-phenyl ether (2.0 g.) in tetrahydrofuran (30 ml.) was added gradually to the magnesium turnings with stirring and heating. After about twenty minutes of external heating to reflux, a self-sustaining reaction was observed. The remaining solution of phenyl ether was then added at a rate to maintain a comfortable reaction. Refluxing with external heating was continued after addition was complete and after one hour, the solution was cooled to room temperature and held under nitrogen. A solution of saccharin pseudo-chloride (1.89 g.) in tetrahydrofuran (40 ml.) was cooled to −78° C. and the previously prepared solution of magnesium bromide reagent was added dropwise to the pseudo-chloride solution under nitrogen. The resulting reaction mixture was stirred cold for about 2 hours and then stirred at room temperature overnight. The reaction mixture was then cooled in an ice water bath and treated with saturated aqueous ammonium chloride solution. The aqueous solution was extracted with chloroform several times and the combined chloroform extracts washed with water and dried over anhydrous sodium sulfate followed by drying over anhydrous calcium sulfate. A colorless oil was obtained which was extracted several times with small portions of light petroleum ether to leave behind a pale yellow tacky tar. The yellow tar was triturated with ether leaving behind an off-white solid. The off-white solid was dissolved in a small amount of chloroform, and the filtrate treated with carbon black and filtered through Celite. Upon removing the solvent, the title compound was obtained as an off-white solid which was dried under vacuum in the presence of $P_2O_5$. Yield 0.520 g.

3-chlorobenz[d]isothiazole-1,1-dioxide (saccharin pseudo-chloride) was prepared as follows:

35 g. of saccharin and 43.7 g. of $PCl_5$ were placed in a bath heated to 170° C. and maintained at this temperature for 1½ hours during which time complete solution occured and $POCl_3$ began to reflux. The $POCl_3$ was removed at reduced pressure to leave a crystalline residue. Diethyl ether was added to the crystalline residue and stirred well. The title compound was recovered as white crystals, 12.5 g. (melting range 146°–147° C.).

EXAMPLE 3

Preparation of the Compound of Formula (3)

(i) Using a syringe, 20.0 mls. of n-butyllithium (2.4 M in hexane) was added dropwise over 1 hour to a solution of 9.16 g. of saccharin (previously dried overnight at 80° C. in vacuo) in 250 mls. of dry tetrahydrofuran under nitrogen at −75° C. to −73° C. with rapid stirring. The reaction solution comprising the N-lithium salt of saccharin in tetrahydrofuran was used directly in step (iii) without isolating the lithium salt.

(ii) In a dried 1 l. flask, 13.86 g. of 4-bromo-2,6-dimethoxy-methylenemethoxyphenyl ether was dissolved in 300 mls. of dry tetrahydrofuran under nitrogen, and 20.83 mls. of n-butyllithium (2.4 M in hexane) was added dropwise with stirring at −75° C. After addition was complete, the reaction solution was stirred at −75° C. for about 30 minutes.

(iii) The solution of saccharin lithium salt prepared in step (i) was transferred to an addition funnel using a double-tip needle under nitrogen pressure and added to the solution of 4-Li-2,6-dimethoxy-methylenemethoxyphenyl ether prepared in step (ii) during about 15 minutes with stirring at a temperature of −75° C. to −70° C. The reaction mixture was stirred for about 2 hours at −75° C. and then warmed to 0° C. during an hour.

(iv) A solution of 5.2 g. of ammonium chloride in 175 mls. of water was added dropwise to the reaction mixture of step (iii) and the reaction mixture transferred to a 1 l. separatory funnel. After the two phases separated, the aqueous phase was removed and the pH was lowered from about 11 to about 6–7 by the dropwise addition of aqueous 5% hydrochloric acid solution. (A color change from yellow to colorless was observed). The aqueous phase was returned to the separatory funnel and extracted with fresh ether (100 mls.). The ether and tetrahydrofuran/hexane extracts were combined, dried over magnesium sulfate overnight, filtered and the solvent removed to give a yellow oil which crystallized. Ether (100 mls.) was added to the crystalline material and the crystalline material was ground under ether in a mortar, filtered, washed with more ether followed by petroleum ether and air dried. A second crop was collected from the filtrate to give a total yield of 13.0 g. of the title compound.

The 4-bromo-2,6-dimethoxy-methylenemethoxyphenyl ether used above was prepared as follows:

To a 3 liter flask was added 300 g. of $P_2O_5$ under nitrogen and 800 ml. of chloroform (previously dried over $P_2O_5$). The mixture was cooled to −15° C. with a dry ice/acetone bath and then 50 g. of 4-bromo-2,6-dimethoxyphenol in 800 ml. of dimethoxymethane was added over a 25 minute period while maintaining the temperature at −15° C. or below. To the resulting reaction mixture was added 1 ml. of conc. sulfuric acid and then the temperature was allowed to come to room temperature. During this time, a tacky mass of $P_2O_5$ developed. The reaction mixture was stirred for 3 hours. TLC indicated that the reaction was complete.

The chloroform was then decanted into 400 ml. of 10% aqueous sodium hydroxide, stirred well and the chloroform layer separated, washed with water, dried over $Na_2SO_4$ and evaporated to leave a light tan solid. The solid was crystallized from n-propanol to give 32.7 g. of 4-bromo-2,6-dimethoxy-methylenemethoxy-phenyl ether as white crystals (melting range 98°–100° C.).

EXAMPLE 4

Preparation of the Compound of Formula (10)

(i) Saccharin (8.79 g.) previously dried in vacuo over $P_2O_5$ was dissolved in 240 ml. of dry tetrahydrofuran in a flame-dried 500 ml. flask, and the solution was then cooled to −75° C. in a dry ice-acetone bath under nitrogen. n-Butyllithium (18.8 ml.; 2.4 M in hexane) was added dropwise to the saccharin solution during 40 minutes with stirring while maintaining the temperature between about −75° C. and −70° C.

(ii) 2'-Tetrahydropyranyl 4-bromo-2,6-dimethoxyphenyl ether (15.23 g.) previously dried in vacuo over $P_2O_5$ was dissolved in 120 ml. of dry tetrahydrofuran in a second flame-dried 500 ml. flask, and the solution was cooled to −75° C. n-Butyllithium (20 ml.; 2.4 M in hexane) was added to the ether solution while maintaining the temperature between about −75° C. and −70° C. After addition was complete, stirring was continued at −75° C. for 30 minutes.

(iii) The solution of the N-lithium salt of saccharin in tetrahydrofuran prepared in step (i) was added to the solution prepared in step (ii) under nitrogen using a double-tipped needle over a period of 15 minutes. During addition the temperature was kept below −70° C. The reaction mixture was stirred at −75° C. for 2 and ¾ hours and then allowed to warm to −10° C.

(iv) A solution of ammonium chloride (5.35 g.) dissolved in 50 ml. of water was added dropwise to the reaction mixture. The pH was lowered to about 8 with cold aqueous 5% HCl, and the mixture was diluted with water to a total volume of 900 ml. The tetrahydrofuran-hexane phase (250 ml.) was separated, dried over anhydrous sodium sulfate, filtered and stripped to dryness leaving a yellow oil. The pH of the aqueous phase was lowered to about 6 with aqueous 5% HCl and extracted with 200 ml. of ether. The ether extract was dried over anhydrous sodium sulfate, filtered and combined with the yellow oil obtained from the original organic phase. A white precipitate formed in a yellow solution. The precipitate was filtered, washed with ether and air-dried to give 8.34 g. of solids which were taken up in 100 ml. of boiling methanol. The methanol solution was cooled in an ice bath, and the precipitate that formed was filtered, washed with methanol-ether to give the title compound as a yellow powder.

The 2'-tetrahydropyranyl 4-bromo-2,6-dimethoxyphenyl ether used above was prepared as follows:

4-Bromo-2,6-dimethoxyphenol (59.0 g.) was dissolved in 280 ml. of dihdropyran (98%) at room temperature. The solution was cooled to 3° C. in an ice-water bath, and five drops of phosphorus oxychloride was added with stirring. After storing the reaction mixture in a refrigerator overnight, white crystals were collected on a filter, washed thoroughly with n-pentane with grinding to give 56.5 g. of the title compound. A sample of the compound was recrystallized by dissolving in 25 ml. of warm chloroform, filtering (warm) and slowly adding 100 ml. of n-pentane. The solution was allowed to stand at room temperature for 10–15 minutes, scratched to induce crystallization and cooled in a refrigerator for 2 hours. The title compound was recovered by filtration, washed with n-pentane and air-dried (melting range 122°–123° C.).

2'-Tetrahydropyranyl 4-bromophenyl ether was prepared as follows:

To 10.5 ml. of dihydropyran containing 2 drops of conc. HCl was added 10 g. of p-bromophenol. (The reaction was exothermic and the temperature rose to 35° C.) After addition was complete, the reaction solution was heated to 50° C. and then allowed to cool for 1 hour with stirring. 20 ml. of ether was added and extracted with 10 ml. of 10% aqueous sodium hydroxide solution to remove acid and any remaining p-bromophenol. The ether layer was dried over anhydrous sodium sulfate and evaporated under reduced pressure to leave an oil. 80 ml. of ethanol was added and the solution was allowed to stand. The white crystals that formed were recovered by filtration and vacuum dried (7.3 g., melting range 59°–60° C.). The mother liquor was reduced to one-half its original volume and cooled. The additional crystals that formed were recovered by filtration and dried to give 2.1 g. or a total yield of 9.4 g. of 2'-tetrahydropyranyl 4-bromophenyl ether.

Tetrahydropyranylation of 4-bromo-1-naphthol was carried out as follows:

4-Bromo-1-naphthol (12.16 g.) was mixed with 250 ml. of dichloromethane at room temperature. To the resulting slurry was added 125 ml. of dihydropyran and then 13 drops of conc. HCl were added. The clear, straw-colored reaction solution was stirred at room temperature for approximately 3 hours, transferred to a separatory funnel, washed with about 400 ml. of aqueous 10% sodium hydroxide and the dichloromethane layer dried over anhydrous sodium sulfate. After drying, the dichloromethane solution was filtered through fresh anhydrous sodium sulfate, and the pale straw filtrate was evaporated under reduced pressure leaving 25.9 g. of straw yellow oil. The oil was applied directly to a wet packed $SiO_2$ column (100–200 mesh: 4/1 petroleum ether/ether) and eluted with 4/1 petroleum ether/ether. Twenty-four fractions of about 50 ml. each were collected, and fractions 9–24 were combined and evaporated to give 16.91 g. of straw syrup which upon standing crystallized to give the title compound as pale lemon crystals.

EXAMPLE 5

Preparation of the Compound of Formula (18)

(a) The 2'-tetrahydropyranyl ether of 4-bromo-1-naphthol (1.0 g.) was dissolved in 20 ml. of anhydrous tetrahydrofuran under nitrogen and cooled to −65° C. To this was added 1.37 ml. of n-butyllithium (2.4 M in hexane). The solution, which turned yellow, was stirred for one hour at −65° C.

(b) Saccharin pseudo-chloride (0.65 g.) was added to 30 ml. of tetrahydrofuran at −65° C. and stirred under nitrogen. To the resulting solution was slowly added the solution prepared in step (a). After addition was complete, the reaction mixture was stirred for one hour at −65° C., poured into water, the pH adjusted to 6 with conc. HCl and extracted with ether. The ether was dried and evaporated. TLC of the residue on silica gel with ether showed some 2:1 product. Crystallization from ethanol gave 0.2 g. of the title compound as light yellow crystals.

The methoxymethyl ether of 4-bromophenol and of 4-bromo-1-naphthol were prepared according to the procedures described in the above examples. The 2'-tetrahydropyranyl ethers of 4-bromo-2,6-diisopropyl-phenol and of 4-bromo-2,6-dichloro-phenol also were prepared according to the procedures described in the above examples.

The dimethyl-t-butylsilyl ether of 4-bromo-1-naphthol was prepared as follows:

4-Bromo-1-naphthol (22.1 g.) and dimethyl-t-butylsilyl chloride (18.1 g.) were dissolved in 50 ml. of dry dimethylformamide at room temperature. The resulting solution was cooled in an ice bath and imidazole (17.0 g.) added under nitrogen. (A slight exotherm was observed.) The reaction mixture was stirred overnight.

The reaction mixture was poured into 1500 ml. of water at about 20° C. with stirring. The pH was adjusted to 4-5 with dilute HCl, and the solids were filtered, washed with water, and air dried for 2 hours and then dissolved in 150 ml. of boiling isopropanol. The isopropanol solution was filtered while hot and then cooled slowly to room temperature. Crystals began to form and after standing at room temperature overnight, the solution was cooled in an ice water bath for 1 hour and filtered. The solid collected was washed with small amounts of isopropanol, air dried briefly and then dried in vacuo for 2 hours to give 24.3 g. of the title compound (melting range 70°–73° C.).

It will be appreciated that the foregoing blocked phenols and blocked 1-naphthols and other blocked 4-bromophenols and 1-naphthols within the scope of the present invention may be converted to the corresponding 4-lithium derivatives and then reacted with the N-lithium salt of saccharin to give the corresponding 3-substituted-benz[d]isothiazole-1,1-dioxides as described in Example 1 above. Alternately, the blocked 4-bromophenols and blocked 4-bromo-1-naphthols may be converted to a Grignard reagent and reacted with saccharin pseudo-chloride to give the corresponding 3-substituted-benz[d]isothiazole-1,1-dioxides as described in Example 2.

As mentioned above, the compounds of the present invention are useful as intermediates in the synthesis of certain 3,3-disubstituted-2,3-dihydrobenz[d]isothiazole-1,1-dioxides possessing a carbonyl group in the 2-position. Such compounds possessing a 4'-hydroxyphenyl moiety as one of the 3,3 substituents and a phenyl/-naphthyl or 4'-substituted phenyl/4'-substituted naphthyl moiety as the other of the 3,3 substituents form the subject matter of copending U.S. patent application Ser. No. 836,021 of Stanley M. Bloom, Alan L. Borror and James W. Foley filed concurrently herewith and of copending U.S. patent application Ser. Nos. 835,998; 836,005; and 836,009 of Stanley M. Bloom, of Alan L. Borror and James W. Foley also filed concurrently herewith. As discussed in the aforementioned applications, compounds may be selected for use as classical pH-sensitive indicator dyes or as photographic optical filter agents and filter agent precursors depending upon the 2-substituent of the benz[d]isothiazole ring. The photographic use of those compounds which may be employed as photographic optical filter agents and filter agent percursors forms the subject matter of copending U.S. patent application Ser. No. 836,006 of Stanley M. Bloom, Alan L. Borror and James W. Foley filed concurrently herewith. The 2,3-dihydrobenz[d]isothiazole-1,1-dioxides possessing a 4'-hydroxynaphthyl moiety as one of the 3,3 substituents and a naphthyl or 4'-substituted naphthyl moiety as the other of the 3,3 substituents form the subject matter of copending U.S.

patent application Ser. No. 836,067 of Alan L. Borror, Louis Cincotta, Ernest W. Ellis and James W. Foley filed concurrently herewith, and as described therein, compounds may be selected for use as classical pH-sensitive indicator dyes or as antihalo dyes in photography.

Since certain changes may be made in the above processes and products without departing from the scope of the invention herein involved, it is intended that all matter contained in the above description shall be interpreted as illustrative and not in a limiting sense.

What is claimed is:

1. A compound of the formula

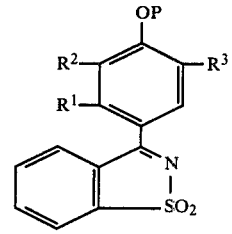

wherein $R^1$ is hydrogen, alkyl having 1 to 4 carbon atoms, alkoxy having 1 to 4 carbon atoms or —OP; $R^2$ and $R^3$ each are hydrogen, alkyl having 1 to 4 carbon atoms, alkoxy having 1 to 4 carbon atoms, chloro or fluoro; $R^1$ and $R^2$ taken together represent the carbon atoms necessary to complete a fused benzene ring; and P is methoxymethyl, 2'-tetrahydropyranyl or dimethyl-t-butylsilyl.

2. A compound as defined in claim 1 wherein P is methoxymethyl.

3. A compound as defined in claim 1 wherein P is 2'-tetrahydropyranyl.

4. A compound as defined in claim 1 wherein P is dimethyl-t-butylsilyl.

5. A compound as defined in claim 1 wherein $R^1$ and $R^2$ each are hydrogen.

6. A compound as defined in claim 1 wherein $R^1$ and $R^2$ taken together represent the carbon atoms necessary to complete a fused benzene ring.

7. A compound as defined in claim 5 wherein $R^3$ is hydrogen.

8. A compound as defined in claim 6 wherein $R^3$ is hydrogen.

9. A compound as defined in claim 1 wherein $R^2$ and $R^3$ each are alkyl.

10. A compound as defined in claim 1 wherein $R^2$ and $R^3$ each are alkoxy.

11. A compound as defined in claim 9 wherein said $R^1$ is hydrogen.

12. A compound as defined in claim 10 wherein said $R^1$ is hydrogen.

13. A compound as defined in claim 11 wherein said $R^2$ and $R^3$ are methyl.

14. A compound as defined in claim 11 wherein said $R^2$ and $R^3$ are isopropyl.

15. A compound as defined in claim 12 wherein said $R^2$ and $R^3$ are methoxy.

16. A compound as defined in claim 7 wherein said P is 2'-tetrahydropyranyl.

17. A compound as defined in claim 15 wherein said P is 2'-tetrahydropyranyl.

18. A compound as defined in claim 15 wherein said P is methoxymethyl.

19. A compound as defined in claim 13 wherein said P is methoxymethyl.

20. A compound as defined in claim 8 wherein said P is dimethyl-t-butylsilyl.

21. A compound as defined in claim 8 wherein said P is methoxymethyl.

22. A compound as defined in claim 8 wherein said P is 2'-tetrahydropyranyl.

23. A compound as defined in claim 7 wherein said P is methoxymethyl.

* * * * *